United States Patent
Dodge et al.

(10) Patent No.: US 10,080,783 B2
(45) Date of Patent: Sep. 25, 2018

(54) INTRAVENTRICULAR ENZYME DELIVERY FOR LYSOSOMAL STORAGE DISEASES

(71) Applicant: Genzyme Corporation, Cambridge, MA (US)

(72) Inventors: James Dodge, Bridgewater, NJ (US); Marco A. Passini, Bridgewater, NJ (US); Lamya Shihabuddin, Bridgewater, NJ (US); Seng H. Cheng, Bridgewater, NJ (US)

(73) Assignee: Genzyme Corporation, Cambridge, MA (US)

(*) Notice: Subject to any disclaimer, the term of this patent is extended or adjusted under 35 U.S.C. 154(b) by 0 days.

(21) Appl. No.: 14/559,851

(22) Filed: Dec. 3, 2014

(65) Prior Publication Data

US 2015/0313970 A1 Nov. 5, 2015

Related U.S. Application Data

(63) Continuation of application No. 12/175,610, filed on Jul. 18, 2008, now Pat. No. 8,926,967, which is a continuation of application No. PCT/US2007/001566, filed on Jan. 22, 2007.

(60) Provisional application No. 60/760,378, filed on Jan. 20, 2006.

(51) Int. Cl.
*A61K 38/46* (2006.01)
*A61K 9/00* (2006.01)
*A61K 38/47* (2006.01)

(52) U.S. Cl.
CPC .......... *A61K 38/465* (2013.01); *A61K 9/0019* (2013.01); *A61K 38/47* (2013.01); *C12Y 301/04012* (2013.01); *C12Y 301/06013* (2013.01); *C12Y 302/0102* (2013.01); *C12Y 302/01045* (2013.01); *C12Y 302/01076* (2013.01); *C12Y 304/14* (2013.01)

(58) Field of Classification Search
None
See application file for complete search history.

(56) References Cited

U.S. PATENT DOCUMENTS

| | | | |
|---|---|---|---|
| 5,670,488 A | 9/1997 | Gregory et al. | |
| 5,720,720 A | 2/1998 | Laske et al. | |
| 5,814,014 A | 9/1998 | Elsberry et al. | |
| 5,882,877 A | 3/1999 | Gregory et al. | |
| 5,994,136 A | 11/1999 | Naldini et al. | |
| 6,013,516 A | 1/2000 | Verma et al. | |
| 6,042,579 A | 3/2000 | Elsberry et al. | |
| 6,689,756 B2 | 2/2004 | Hesson et al. | |
| 8,926,967 B2 | 1/2015 | Dodge et al. | |
| 2002/0130079 A1 | 12/2002 | Lerner | |
| 2002/0183683 A1 | 12/2002 | Lerner | |
| 2003/0022879 A1 | 1/2003 | Hesson et al. | |
| 2003/0163181 A1 | 8/2003 | Frazer et al. | |
| 2004/0105888 A1 | 5/2004 | Pratt | |
| 2004/0258666 A1 | 12/2004 | Passini et al. | |
| 2005/0026823 A1 | 2/2005 | Zankel et al. | |
| 2005/0048047 A1 | 5/2005 | Kakkis | |
| 2005/0102708 A1 | 5/2005 | Lecanu et al. | |
| 2005/0208090 A1 | 9/2005 | Keimel et al. | |
| 2009/0105141 A1 | 4/2009 | Dodge | |
| 2009/0123451 A1 | 5/2009 | Dodge et al. | |
| 2009/0130079 A1 | 5/2009 | Dodge et al. | |
| 2010/0173979 A1 | 7/2010 | Dodge et al. | |
| 2015/0313970 A1 | 11/2015 | Dodge et al. | |

FOREIGN PATENT DOCUMENTS

| | | |
|---|---|---|
| EP | 0 130 166 A1 | 12/1991 |
| JP | 2009-525963 A | 7/2009 |
| RU | 2179034 C2 | 2/2002 |
| WO | WO-95/29993 A1 | 11/1995 |
| WO | WO-96/33280 A1 | 10/1996 |
| WO | WO-96/40955 A1 | 12/1996 |
| WO | WO-97/00326 A1 | 1/1997 |
| WO | WO-97/25446 A1 | 7/1997 |
| WO | WO-98/11206 A2 | 3/1998 |
| WO | WO 99/57296 A1 | 11/1999 |
| WO | WO-2005/002515 A2 | 1/2005 |
| WO | WO-2005/002515 A3 | 1/2005 |
| WO | WO-2005/021064 A2 | 3/2005 |
| WO | WO-2005/021064 A3 | 3/2005 |
| WO | WO-2005/072049 A2 | 8/2005 |
| WO | WO-2005/095955 A1 | 10/2005 |
| WO | WO-2007/084737 A2 | 7/2007 |
| WO | WO-2007/084737 A3 | 7/2007 |
| WO | WO-2007/095056 A2 | 8/2007 |
| WO | WO-2007/095056 A3 | 8/2007 |

OTHER PUBLICATIONS

Bembi et al. "Cerebrospinal Fluid infusion of Alglucerase in the Treatment of Acute Neuronopathic Gauche's Disease," *Pediatric Research*, 38(3), 1995, Author Index p. 464. Abstract #14.
Belichenko, P.V. et al., Penetration, diffusion, and uptake of recombinant human e-L-iduronidase after intraventricular injection into the rat brain, *Molecular Genetics and Metaboiisrn* 86:141-149, 2005.
Chang, M. et al, "Gene Therapy and Enzyme Replacement in a Mouse Model ref LateInfanNe N lipoiusdnosio", Molecular Therapy, #218, 12(S1) S841, May 2006.
Chian et al., "IGE-1:Tetanus Toxin Fragment C Fusion Protein Improves Delivery of 1GF-1 to Spinal Cord but Fails to Prolong Survival of ALS Mice", *Brain Research*, 1287:1-19, 2009.

(Continued)

*Primary Examiner* — Kade Ariani
(74) *Attorney, Agent, or Firm* — Morrison & Foerster LLP

(57) ABSTRACT

Lysosomal storage diseases can be successfully treated using intraventricular delivery of the enzyme which is etiologically deficient in the disease. The administration can be performed slowly to achieve maximum effect. Surprisingly, effects are seen on both sides of the blood-brain barrier, making this an ideal delivery means for lysosomal storage diseases which affect both brain and visceral organs.

22 Claims, 11 Drawing Sheets

Specification includes a Sequence Listing.

(56) References Cited

OTHER PUBLICATIONS

Dodge, J.C. et al. (2009, Nov. 14, 2008). "Intracerebroventricular Infusion of Acid Sphingomyelinase Corrects CNS Manifestations in a Mouse Model of Niemann-Pick A Disease," *Experimental Neurology* 215:394-357.
Dore, S. at al., "Rediscovering an Old Friend, iG.F-1: Potential Use in the Treatment Neurodegenerative Diseases", *Trends in Neurosciences*, 20(4326-331 1997.
European Office Action dated Jun. 26, 2012, for EP Application No. 07750236.7, filed on Feb. 8, 2007, four pages.
European Office Action dated Dec. 23, 2010, for EP Application No. 07750236.7, filed on Feb. 8, 2007, six pages.
Franz, C.F. et at,, "Intraspinal Cord Delivery of IGF-1 Mediated by Adeno Associated Virus 2 is Neuroprotective in a Rat Modle of Familial ALS," *Neurobiology of Disease* 33: 2009, 473-481.
Godel, V. et al. (1978). "Visual Functions in Tay Sachs Diseased Patients Following Enyzme Replacement Therapy," *Metab. Ophthalmol.* 2:27-32.
Grondin, R. at al, "Chronic, Controlled GDNF Infusion Promotes Structual and Functional Recovery in Advanced Parkinsonian Monkeys", *Brain*, 125:2191-2201, 2002.
Horinouchi, K. et al., "Acid Sphingomyelinase Deficient Mice: a Model of Types A and B Niemann-Pick Disease", *Nature Genetics*, 10:288-293, Jul. 1995.
International Search Report from PCT/US2007/01599, dated Sep. 26, 2008, 1 page.
International Search Report from PCT/US2007/01566, dated Nov. 16, 2007, 2 pages.
International Search Report from PCT/US2007/03382, dated Oct. 16, 2007, 1 page.
Jin, H-K. et al. (Dec. 2003). "Ex Vivo Gene Therapy Using Bone Marrow-Derived Cells: Combines Effects of Intracerebral and Intravenous Transplantation in a Mouse Model of Niemann-Pick Disease," *Molecular Therapy* 8(6):876-885.
Kakkis, E. et al,, "Intrathesal enzyme, replacement therapy reduces lysomal storage in the Brain and meninges of the canine models of MPS1," molecular Genetics and Metabolism 83:163-174 2004.
Kaspar , K. et al, Retrograde Viral Deliv3ry of IGF-1 Prolongs survival in a Mouse ALS Model, Science, 301:839-842, Aug. 5, 2003.
Lonser, R. at al., "Convection Perfusion of Glucocerebrse for Neuronapathic Gauche Disease", Ann Neurology 57:542-548, 2005.
MacAuley, S.L. et al. (2009, e-pub. Apr. 8, 2009). "Promising CNS-Directed Enzyme Replacement Therapy for Lysosomal Storage Diseases," *Experimental Neurology* 218:5-8.
Miranda, S. et al., "Infusion of Recombinant human Acid Sphingomyelinase into Niemann-Pick disease Mice Leads to Visceral, but not Neurological, Correction of the Pathophysiology", *The FASEB Journal*, 14:1988-1995, Oct. 2000.
Nagaraja,T.N. et al., "In Normal Rat, Intraventricularly Administered Insutin-Like Growth Factor is Rapidly Cleared from CSF with Limited Distribution into Brain" *Cerebrospinal Fluid Research*, 2(5):1-15. (Jul. 26, 2005).
NPL Search Results, Oct. 8, 2013, 1 page.
Qiu et al., "Activation of Human Acid Sphingomyelinase through Modification or Deletion of C-terminal Cysteine", *The Journal of Biological Chemistry*, 278(35):32744-32752, Aug. 2003.
Schuchman, E. et at. Human Acid Sphingomyelinase, *The Journal of Biotogloal Chemistry*, 286(13):8531-8539, May 5, 1991.
Shen et al. 2004 "Principles and Applicability of CSF Sampling for the Assessment of CNS Drug Delivery and Pharmacodynamics," *Advanced Drug Delivery Reviews* 56:1825-1857.
Sorensen, E.J.. et al., "Subcutaneous IGF-1 is Not Beneficial in 2-year ALS Trial," *Neurology* 71: 770-1776, Nov. 25, 2008.
Stedman's Medical Dictionary, 26th edition, 1995, p. 1951.
Von Specht, B.U. et al. (Jun. 1979). "Enzyme Replacement in Tay-Sachs Disease," *Neurology* 29:848-854.
Written Opinion from PCT/US2007/01599, dated Sep. 26, 2008, 6 pages.
Written Opinion from PCT/US2007/01566, dated Nov. 16, 2007, 6 pages.
Written Opinion from PCT/US2007/03382, dated Oct. 16, 2007, 5 pages.
Ziegler, R.J. et al. (2011, e-pub. Jul. 14, 2011). "Distribution of Acid Sphingomyelinase in Rodent and Non-Human Primate Brain After Intracerebroventricular Infusion," *Experimental Neurology* 231:261-271.
Abruzzese, R.V. et al. (Jun. 10, 1999). "Ligand-Dependent Regulation of Plasmid-Based Transgene Expression in Vivo," *Hum. Gene Ther.* 10(9):1499-1507.
Berkner, K.L. (1992). "Expression of Heterologous Sequences in Adenoviral Vectors," *Curr. Top Micro. and Immunol.*158:39-66.
Bijvoet, A.G. et al. (Jan. 1998). "Generalized Glycogen Storage and Cardiomegaly in a Knockout Mouse Model of Pompe Disease," *Hum. Mol. Genet.* 7(1):53-62.
Cho, S.K. et al. (2005). "Characterization of Lipid-Linked Oligosaccharide Accumulation in Mouse Models of Batten Disease," *Glycobiology* 15(6):637-648.
Clarke, L.A. et al. (1997). "Murine Mucopolysaccharidosis Type I: Targeted Disruption of the Murine α-L-Iduronidase Gene," *Hum. Mol. Genet.* 6(4):503-511.
Final Office Action dated Apr. 23, 2014, for U.S. Appl. No. 12/175,610, filed Jul. 18, 2008, 5 pages.
Final Office Action dated Sep. 1, 2010, for U.S. Appl. No. 12/175,610, filed Jul. 18, 2008, 17 pages.
Final Office Action dated Feb. 10, 2017, for U.S. Appl. No. 12/187,896, filed Aug. 7, 2008, 7 pages.
Final Office Action dated Jan. 16, 2015, for U.S. Appl. No. 12/187,896, filed Aug. 7, 2008, 9 pages.
Final Office Action dated Dec. 9, 2010, for U.S. Appl. No. 12/187,896, filed Aug. 7, 2008, 11 pages.
Fisher, K.J. et al. (Mar. 1, 1996). "Recombinant Adenovirus Deleted of All Viral Genes for Gene Therapy of Cystic Fibrosis," *Virology* 217(1):11-22.
Jin, H. K. et al. (May 1, 2002). "Intracerebral Transplantation of Mesenchymal Stem Cells into Acid Sphingomyelinase-Deficient Mice Delays the Onset of Neurological Abnormalities and Extends Their Life Span," *J. Clin. Invest.* 109(9):1183-1191.
Jolly, D. (Mar. 1994). "Viral Vector Systems for Gene Therapy," *Cancer Gene Therapy* 1(1):51-64.
Katz, M.L. et al. (Aug. 1999). "A Mouse Gene Knockout Model for Juvenile Ceroid-Lipofuscinosis (Batten Disease)," *J. Neurosci. Res.* 57(4):551-556.
Kochanek, S.et al. (Jun. 1996). "A New Adenoviral Vector: Replacement of All Viral Coding Sequences with 28 Kb of DNA Independently Expressing Both Full-Length Dystrophin and Beta-Galactosidase," *Proc. Natl. Acad. Sci. USA* 93(12):5731-5736.
Kotin, R. M. et al. (Mar. 1, 1990). "Site-Specific Integration by Adeno-Associated Virus," *Proc. Natl. Acad. Sci.* 87(6):2211-2215.
Leventhal, A.R. et al. (Nov. 30, 2001). "Acid Sphingomyelinase-Deficient Macrophages Have Defective Cholesterol Trafficking and Efflux," *J. Biol. Chem.* 276(48):44976-44983.
Lieber, A. et al. (Dec. 1996). "Recombinant Adenoviruses with Large Deletions Generated by Cre-Mediated Excision Exhibit Different Biological Properties Compared with First-Generation Vectors In Vitro and In Vivo," *J. Virol.* 70(12):8944-8960.
Menon, K.P. et al. (Nov. 1992). "Architecture of the Canine IDUA Gene and Mutation Underlying Canine Mucopolysaccharidosis I," *Genomics* 14(3):763-768.
Miller, A.D. (Jun. 11, 1992). "Human Gene Therapy Comes of Age" Nature 357(6378):455-460.
Morral, N. et al. (Dec. 10, 1998). "High Doses of a Helper-Dependent Adenoviral Vector Yield Supraphysiological Levels of α1-Antitrypsin with Negligible Toxicity," *Hum. Gene Ther.* 9(18):2709-2716.
Muenzer, J. et al. (2002). "Enzyme Replacement Therapy in Mucopolysaccharidosis Type II (Hunter syndrome): A Preliminary Report," *Acta Pædiatr Suppl* 439:98-99.
Muzyczka, N. (1992). "Use of Adeno-Associated Virus as a General Transduction Vector for Mammalian Cells," *N. Curr. Top. Micro. Immunol.* 158:97-129.

(56) References Cited

OTHER PUBLICATIONS

Non-Final Office Action dated Mar. 5, 2010, for U.S. Appl. No. 12/175,610, filed Jul. 18, 2008, 13 pages.
Non-Final Office Action dated Oct. 16, 2013, for U.S. Appl. No. 12/175,610, filed Jul. 18, 2008, 9 pages.
Non-Final Office Action dated Apr. 21, 2016, for U.S. Appl. No. 12/187,896, filed Aug. 7, 2008, 7 pages.
Non-Final Office Action dated Jun. 20, 2014, for U.S. Appl. No. 12/187,896, filed Aug. 7, 2008, 9 pages.
Non-Final Office Action dated Mar. 30, 2010, for U.S. Appl. No. 12/187,896, filed Aug. 7, 2008, 12 pages.
Otterbach, B. et al. (Jun. 30, 1995). "Acid Sphingomyelinase-Deficient Mice Mimic the Neurovisceral Form of Human Lysosomal Storage Disease (Niemann-Pick Disease)," *Cell* 81(7):1053-1061.
Parks, R.J. et al. (Nov. 26, 1996). A Helper-Dependent Adenovirus Vector System: Removal of Helper Virus by Cre-Mediated Excision of the Viral Packaging Signal, *Proc. Natl. Acad. Sci. USA* 93(24):13565-13570.
Ponnazhagan, S. et al. (Feb. 10, 1997). "Lack of Site-Specific Integration of the Recombinant Adeno-Associated Virus 2 Genomes in Human Cells," *Hum Gene Ther.* 8(3):275-284.
Raben, N. et al. (Oct. 2003). "Enzyme Replacement Therapy in the Mouse Model of Pompe Disease" *Mol. Genet. Metab.* 80(1-2):159-169.
Restriction Requirement dated Sep. 3, 2009, for U.S. Appl. No. 12/175,610, filed Jul. 18, 2008, 6 pages.
Sano, Y. (Dec. 10, 1988). "Morphological Aspects of the Blood-Brain Barrier—A Historical Review," *Advances in Neurological Sciences* 32(6):953-965. (English Abstract Only).
Schuchman, E. et al. (2001). "Niemann-Pick Disease Types A and B: Acid Sphingomyelinase Deficiencies," Chapter 144 in *The Metabolic and Molecular Bases of Inherited Diseases*, Scriver, et al. eds., McGraw-Hill, pp. 3589-3610.
Slotte, J.P. (1997). "Cholesterol-Sphingomyelin Interactions In Cells—Effects on Lipid Metabolism," *Subcell. Biochem.* 28:277-293.
Stedman, T. L. (1995). *Stedman's Medical Dictionary*, Williams & Wilkins Baltimore 26:220, 1 page.
Viana, M.B. et al. (1990). "Very Low Levels of High Density Lipoprotein Cholesterol in Four Sibs of a Family with Non-Neuropathic Niemann-Pick disease and Sea-Blue Histiocytosis," *J. Med. Genet.* 27:499-504.
Xu, Y. et al. (Nov. 2003). "Viable Mouse Models of Acid β-Glucosidase Deficiency: The Defect in Gaucher Disease," *Am. J. Pathol.* 163(5):2093-2101.
Non-Final Office Action dated Aug. 4, 2017, for U.S. Appl. No. 12/187,896, filed Aug. 7, 2008, 7 pages.
Final Office Action dated Feb. 22, 2018, for U.S. Appl. No. 12/187,896, filed Aug. 7, 2008, 7 pages.

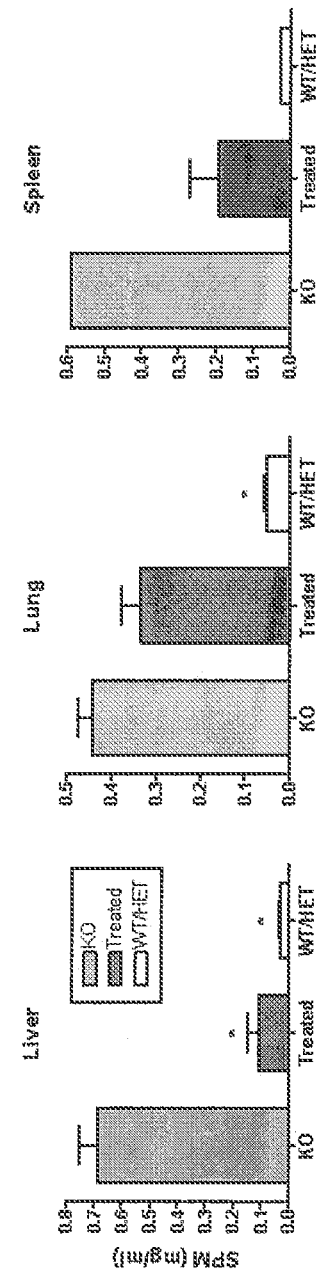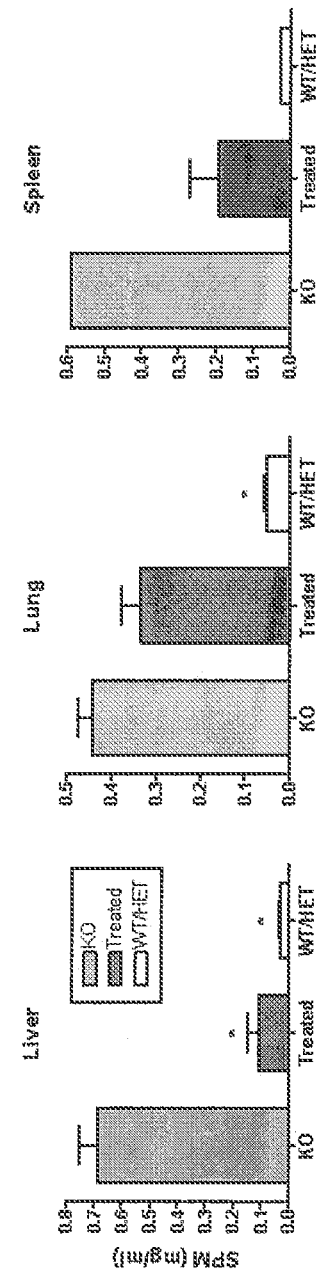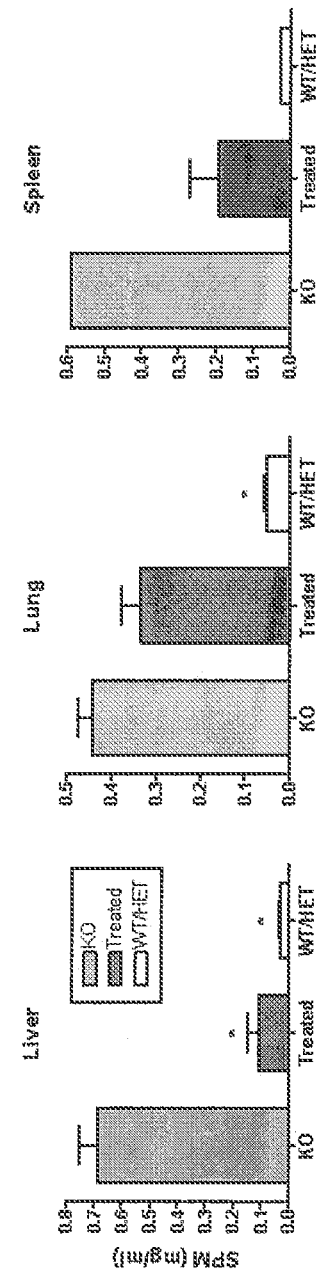

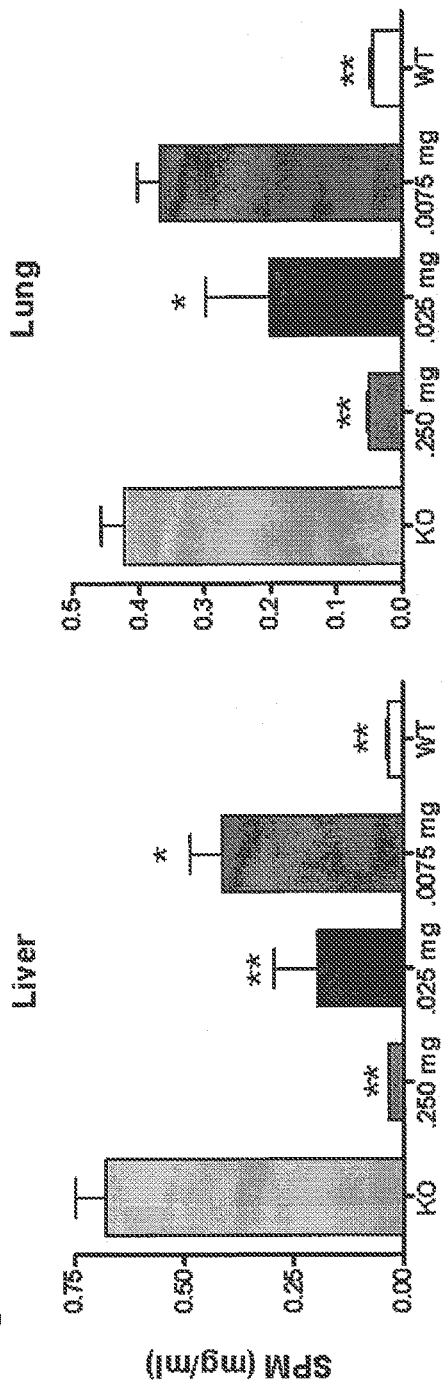
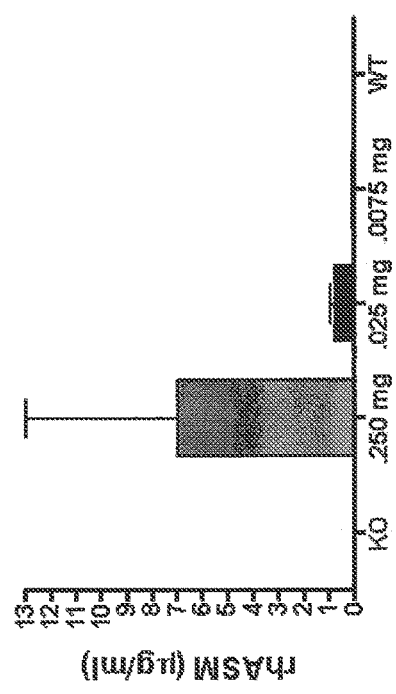
Fig. 6A Liver
Fig. 6B Lung
Fig. 6C hASM serum levels

FIG. 7.

| | | Known | variants | | | |
|---|---|---|---|---|---|---|
| VARIANT | 157 | 157 | 1 | C -> R | (seems to be less active). |
| VARIANT | 242 | 242 | 1 | G -> R | (in NPB). |
| VARIANT | 246 | 246 | 1 | E -> Q | (in NPA; 30% residual activity). |
| VARIANT | 248 | 248 | 1 | S -> R | (in NPA). |
| VARIANT | 302 | 302 | 1 | L -> P | (in NPA; in 23% of NPA Ashkenazi Jewish patients). |
| VARIANT | 319 | 319 | 1 | H -> Y | (in NPA). |
| VARIANT | 371 | 371 | 1 | P -> S | (in NPB). |
| VARIANT | 382 | 382 | 1 | M -> I | (in NPA). |
| VARIANT | 383 | 383 | 1 | N -> S | (in NPB). |
| VARIANT | 389 | 389 | 1 | N -> T | (in NPA). |
| VARIANT | 391 | 391 | 1 | W -> G | (in NPB; low sphingomyelin degradation rates). |
| VARIANT | 421 | 421 | 1 | H -> Y | (in NPB). |
| VARIANT | 436 | 436 | 1 | S -> R | (in NPB). |
| VARIANT | 446 | 446 | 1 | Y -> C | (in NPA). |
| VARIANT | 463 | 463 | 1 | F -> S | (in NPA). |
| VARIANT | 475 | 475 | 1 | P -> L | (in NPA). |
| VARIANT | 496 | 496 | 1 | R -> L | (in NPA; in 32% of NPA Ashkenazi Jewish patients). |
| VARIANT | 537 | 537 | 1 | Y -> H | (in NPA). |
| VARIANT | 577 | 577 | 1 | G -> S | (in NPA). |
| VARIANT | 608 | 608 | 1 | Missing | (in NPB; prevalent among NPB patients from the North-African Maghreb region). |

SEQUENCE LISTING

```
<160> NUMBER OF SEQ ID NOS: 1

<210> SEQ ID NO 1
<211> LENGTH: 629
<212> TYPE: PRT
<213> ORGANISM: Homo sapiens

<400> SEQUENCE: 1

Met Pro Arg Tyr Gly Ala Ser Leu Arg Gln Ser Cys Pro Arg Ser Gly
1               5                   10                  15

Arg Glu Gln Gly Gln Asp Gly Thr Ala Gly Ala Pro Gly Leu Leu Trp
            20                  25                  30

Met Gly Leu Val Leu Ala Leu Ala Leu Ala Leu Ala Leu Ala Leu Ser
        35                  40                  45

Asp Ser Arg Val Leu Trp Ala Pro Ala Glu Ala His Pro Leu Ser Pro
    50                  55                  60

Gln Gly His Pro Ala Arg Leu His Arg Ile Val Pro Arg Leu Arg Asp
65                  70                  75                  80

Val Phe Gly Trp Gly Asn Leu Thr Cys Pro Ile Cys Lys Gly Leu Phe
                85                  90                  95

Thr Ala Ile Asn Leu Gly Leu Lys Lys Glu Pro Asn Val Ala Arg Val
            100                 105                 110

Gly Ser Val Ala Ile Lys Leu Cys Asn Leu Leu Lys Ile Ala Pro Pro
        115                 120                 125

Ala Val Cys Gln Ser Ile Val His Leu Phe Glu Asp Asp Met Val Glu
    130                 135                 140

Val Trp Arg Arg Ser Val Leu Ser Pro Ser Glu Ala Cys Gly Leu Leu
145                 150                 155                 160

Leu Gly Ser Thr Cys Gly His Trp Asp Ile Phe Ser Ser Trp Asn Ile
                165                 170                 175

Ser Leu Pro Thr Val Pro Lys Pro Pro Lys Pro Pro Ser Pro Pro
            180                 185                 190

Ala Pro Gly Ala Pro Val Ser Arg Ile Leu Phe Leu Thr Asp Leu His
        195                 200                 205

Trp Asp His Asp Tyr Leu Glu Gly Thr Asp Pro Asp Cys Ala Asp Pro
    210                 215                 220

Leu Cys Cys Arg Arg Gly Ser Gly Leu Pro Pro Ala Ser Arg Pro Gly
225                 230                 235                 240

Ala Gly Tyr Trp Gly Glu Tyr Ser Lys Cys Asp Leu Pro Leu Arg Thr
                245                 250                 255

Leu Glu Ser Leu Leu Ser Gly Leu Gly Pro Ala Gly Pro Phe Asp Met
            260                 265                 270

Val Tyr Trp Thr Gly Asp Ile Pro Ala His Asp Val Trp His Gln Thr
        275                 280                 285
```

-continued

```
Arg Gln Asp Gln Leu Arg Ala Leu Thr Thr Val Thr Ala Leu Val Arg
            290                 295                 300
Lys Phe Leu Gly Pro Val Pro Val Tyr Pro Ala Val Gly Asn His Glu
305                 310                 315                 320
Ser Thr Pro Val Asn Ser Phe Pro Pro Pro Phe Ile Glu Gly Asn His
                325                 330                 335
Ser Ser Arg Trp Leu Tyr Glu Ala Met Ala Lys Ala Trp Glu Pro Trp
            340                 345                 350
Leu Pro Ala Glu Ala Leu Arg Thr Leu Arg Ile Gly Gly Phe Tyr Ala
            355                 360                 365
Leu Ser Pro Tyr Pro Gly Leu Arg Leu Ile Ser Leu Asn Met Asn Phe
            370                 375                 380
Cys Ser Arg Glu Asn Phe Trp Leu Leu Ile Asn Ser Thr Asp Pro Ala
385                 390                 395                 400
Gly Gln Leu Gln Trp Leu Val Gly Glu Leu Gln Ala Ala Glu Asp Arg
                405                 410                 415
Gly Asp Lys Val His Ile Ile Gly His Ile Pro Pro Gly His Cys Leu
            420                 425                 430
Lys Ser Trp Ser Trp Asn Tyr Tyr Arg Ile Val Ala Arg Tyr Glu Asn
            435                 440                 445
Thr Leu Ala Ala Gln Phe Phe Gly His Thr His Val Asp Glu Phe Glu
    450                 455                 460
Val Phe Tyr Asp Glu Glu Thr Leu Ser Arg Pro Leu Ala Val Ala Phe
465                 470                 475                 480
Leu Ala Pro Ser Ala Thr Thr Tyr Ile Gly Leu Asn Pro Gly Tyr Arg
                485                 490                 495
Val Tyr Gln Ile Asp Gly Asn Tyr Ser Arg Ser Ser His Val Val Leu
            500                 505                 510
Asp His Glu Thr Tyr Ile Leu Asn Leu Thr Gln Ala Asn Ile Pro Gly
        515                 520                 525
Ala Ile Pro His Trp Gln Leu Leu Tyr Arg Ala Arg Glu Thr Tyr Gly
        530                 535                 540
Leu Pro Asn Thr Leu Pro Thr Ala Trp His Asn Leu Val Tyr Arg Met
545                 550                 555                 560
Arg Gly Asp Met Gln Leu Phe Gln Thr Phe Trp Phe Leu Tyr His Lys
                565                 570                 575
Gly His Pro Pro Ser Glu Pro Cys Gly Thr Pro Cys Arg Leu Ala Thr
            580                 585                 590
Leu Cys Ala Gln Leu Ser Ala Arg Ala Asp Ser Pro Ala Leu Cys Arg
            595                 600                 605
His Leu Met Pro Asp Gly Ser Leu Pro Glu Ala Gln Ser Leu Trp Pro
    610                 615                 620
Arg Pro Leu Phe Cys
625
```

INTRAVENTRICULAR ENZYME DELIVERY FOR LYSOSOMAL STORAGE DISEASES

CROSS REFERENCE TO RELATED APPLICATIONS

This application is a continuation of U.S. patent application Ser. No. 12/175,610, filed Jul. 18, 2008, which is a continuation of PCT/US2007/001566, filed Jan. 22, 2007, which claims the benefit under 35 USC § 119(e) of U.S. Provisional Application No. 60/760,378, filed Jan. 20, 2006, each of which is incorporated herein by reference in its entirety for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 159792009602SeqList.txt, date recorded: Dec. 3, 2014, size: 6 KB).

TECHNICAL FIELD OF THE INVENTION

This invention is related to the area of lysosomal storage diseases. In particular, it relates to the treatment and/or prevention of these diseases by enzyme replacement therapy.

SUMMARY OF THE INVENTION

A group of metabolic disorders known as lysosomal storage diseases (LSDs) includes over forty genetic disorders, many of which involve genetic defects in various lysosomal hydrolases. Representative lysosomal storage diseases and the associated defective enzymes are listed in Table 1.

TABLE 1

| Lysosomal storage disease | Defective enzyme |
|---|---|
| Aspartylglucosaminuria | Aspartylglucosaminidase |
| Fabry | alpha.-Galactosidase A |
| Infantile Batten Disease* (CNL1) | Palmitoyl Protein Thioesterase |
| Classic Late Infantile Batten Disease* (CNL2) | Tripeptidyl Peptidase |
| Juvenile Batten Disease* (CNL3) | Lysosomal Transmembrane Protein |
| Batten, other forms* (CNL4-CNL8) | Multiple gene products |
| Cystinosis | Cysteine transporter |
| Farber | Acid ceramidase |
| Fucosidosis | Acid .alpha.-L-fucosidase |
| Galactosidosialidosis | Protective protein/cathepsin A |
| Gaucher types 1, 2*, and 3* | Acid .beta.-glucosidase, or Acid .beta.-galactosidase |
| G.sub.M1 gangliosidosis* | Acid .beta.-galactosidase |
| Hunter* | Iduronate-2-sulfatase |
| Hurler-Scheie* | alpha.-L-Iduronidase |
| Krabbe* | Galactocerebrosidase . |
| alpha.-Mannosidosis* | Acid .alpha.-mannosidase . |
| beta.-Mannosidosis* | Acid .beta.-mannosidase |
| Maroteaux-Lamy | Arylsulfatase B |
| Metachromatic leukodystrophy* | Arylsulfatase A |
| Morquio A | N-Acetylgalactosamine-6-sulfate |
| Morquio B | Acid .beta.-galactosidase |
| Mucolipidosis II/III* | N-Acetylglucosamine-1- |
| Niemann-Pick A*, B | Acid sphingomyelinase |
| Niemann-Pick C* | NPC-1 |
| Pompe* Acid | .alpha.-glucosidase |

TABLE 1-continued

| Lysosomal storage disease | Defective enzyme |
|---|---|
| Sandhoff* | .beta.-Hexosaminidase B |
| Sanfilippo A* | Heparan N-sulfatase |
| Sanfilippo B* | .alpha.-N-Acetylglucosaminidase |
| Sanfilippo C* | Acetyl-CoA: alpha.-glucosaminide |
| Sanfilippo D* | N-Acetylglucosamine-6-sulfate |
| Schindler Disease* | .alpha.-N-Acetylgalactosaminidase |
| Schindler-Kanzaki . | alpha.-N-Acetylgalactosaminidase |
| Sialidosis | .alpha.-Neuramidase |
| Sly* | .beta.-Glucuronidase |
| Tay-Sachs* | .beta.-Hexosaminidase A |
| Wolman* | Acid Lipase |

*CNS involvement

The hallmark feature of LSDs is the abnormal accumulation of metabolites in the lysosomes which leads to the formation of large numbers of distended lysosomes in the perikaryon. A major challenge to treating LSDs (as opposed to treating an organ specific enzymopathy, e.g., a liver-specific enzymopathy) is the need to reverse lysosomal storage pathology in multiple separate tissues. Some LSDs can be effectively treated by intravenous infusion of the missing enzyme, known as enzyme replacement therapy (ERT). For example, Gaucher type 1 patients have only visceral disease and respond favorably to ERT with recombinant glucocerebrosidase (Cerezyme™, Genzyme Corp.). However, patients with metabolic disease that affects the CNS (e.g., type 2 or 3 Gaucher disease) only respond partially to intravenous ERT because the replacement enzyme is prevented from entering the brain by the blood brain barrier (BBB). Furthermore, attempts to introduce a replacement enzyme into the brain by direct injection have been limited in part due to enzyme cytotoxicity at high local concentrations and limited parenchymal diffusion rates in the brain (Partridge, Peptide Drug Delivery to the Brain, Raven Press, 1991).

One exemplary LSD, is Niemann-Pick disease type A (NPA). According to UniProtKB/Swiss-Prot entry P17405, defects in the SMPD1 gene, located on chromosome 11, (11p15.4-p15.1), are the cause of Niemann-Pick disease type A (NPA), also referred to as the classical infantile form of the disease. Niemann-Pick disease is a clinically and genetically heterogeneous recessive disorder. It is caused by the accumulation of sphingomyelin and other metabolically related lipids in the lysosomes, resulting in neurodegeneration starting from early life. Patients may show xanthomas, pigmentation, hepatosplenomegaly, lymphadenopathy and mental retardation. Niemann-Pick disease occurs more frequently among individuals of Ashkenazi Jewish ancestry than in the general population. NPA is characterized by very early onset in infancy and a rapidly progressive course leading to death by three years. The acid sphingomyelinase enzyme (ASM) that is defective in NPA converts sphingomyelin to ceramide. ASM also has phospholipase C activities toward 1,2-diacylglycerolphosphocholine and 1,2-diacylglycerophosphoglycerol. The enzyme converts Sphingomyelin+$H_2O$→N-acylsphingosine+choline phosphate.

In accordance with the present invention, lysosomal storage diseases such as any of the diseases identified in Table 1 above, e.g., Niemann-Pick disease type A or B, are treated and/or prevented using intraventricular delivery to the brain of the enzyme which is etiologically deficient in the disease. The administration can be performed slowly to achieve maximum effect. Effects are seen on both sides of the blood-brain barrier, making this a useful delivery means for lysosomal storage diseases which affect the brain and/or visceral organs. In a first aspect, the invention thus provides for a method of treating or preventing a lysosomal storage disease in patient, which disease is caused by an enzyme deficiency, the method comprising administering the enzyme to the patient via intraventricular delivery to the brain. In a related aspect, the invention provides for the use of an enzyme for the manufacture of a medicament for the treatment or prevention of a lysosomal storage disease in a patient, which disease is caused by a deficiency of the enzyme in the patient, wherein the treatment or prevention comprises the intraventricular administration of the enzyme to the brain. The enzyme deficiency may be caused by e.g., a defect in the expression of the enzyme or by a mutation in the enzyme which leads to a reduced level of activity (e.g., the enzyme being inactive) or an increased rate of clearance/breakdown of the enzyme in vivo. The deficiency may lead to an accumulation of an enzyme's substrate and the administration of the enzyme may lead to a reduction in the level of the substrate in the brain. The lysosomal storage disease may be any of the diseases identified in Table 1 above. The enzyme may be a lysosomal hydrolase.

According to one embodiment of the invention, a patient with Niemann-Pick A or B disease is treated. An acid sphingomyelinase is administered to the patient via intraventricular delivery to the brain in an amount sufficient to reduce sphingomyelin levels in said brain.

Another aspect of the invention is a kit for treating or preventing a lysosomal storage disease in patient, which disease is caused by an enzyme deficiency. The kit comprises the enzyme that is deficient, and a catheter and/or pump for delivery of the enzyme to one or more ventricles in the brain. The catheter and/or pump may be specifically designed and/or adapted for intraventricular delivery. According to one embodiment, the invention provides a kit for treating a patient with Niemann-Pick A or B disease. The kit comprises an acid sphingomyelinase, and a catheter for delivery of said acid sphingomyelinase to the patient's brain ventricles.

Yet another aspect of the invention is a kit for treating a patient with Niemann-Pick A or B disease. The kit comprises an acid sphingomyelinase and a pump for delivery of said acid sphingomyelinase to the patient's brain ventricles.

According to the invention, a patient can be treated who has a lysosomal storage disease which is caused by an enzyme deficiency which leads to accumulation of the enzyme's substrate. Such diseases include Gaucher disease, MPS I and II disease, Pompe disease, and Batten disease (CLN2), among others. The enzyme defective in the particular disease is administered to the patient via intraventricular delivery to the brain. It may be administered to the lateral ventricles and/or to the fourth ventricle. The rate of administration of the enzyme in accordance with the present invention is such that the administration of a single dose may be as a bolus or may take about 1-5 minutes, about 5-10 minutes, about 10-30 minutes, about 30-60 minutes, about 1-4 hours, or consumes more than four, five, six, seven, or eight hours. Substrate levels in said brain may thereby be reduced. The administration of a single dose may take more than 1 minute, more than 2 minutes, more than 5 minutes, more than 10 minutes, more than 20 minutes, more than 30 minutes, more than 1 hour, more than 2 hours, or more than 3 hours.

These and other embodiments which will be apparent to those of skill in the art upon reading the specification provide the art with methods and kits for the treatment and/or prevention of lysosomal storage diseases, in particular those involving both CNS and visceral pathologies.

BRIEF DESCRIPTION OF THE DRAWINGS

FIGS. 3A, 3B, and 3C shows intraventricular administration of rhASM reduces SPM levels in the ASMKO liver (FIG. 3A), spleen (FIG. 3C), and lung (FIG. 3B).

FIGS. 6A, 6B, and 6C shows that intraventricular infusion of rhASM over a 6 h period reduces SPM levels in ASMKO liver (FIG. 6A), serum (FIG. 6C), and lung (FIG. 6B).

FIG. 7 shows documented hASM variants and their relationship to disease or enzyme activity.

DETAILED DESCRIPTION OF THE INVENTION

Figure 1:
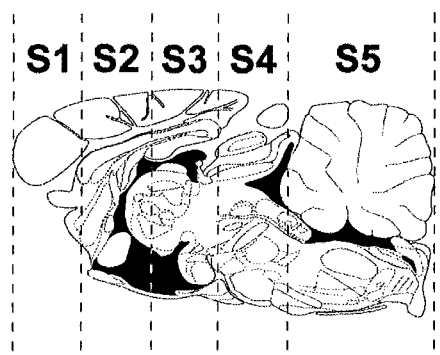
FIG. 1 shows diagram of sections of brain that were analyzed for sphingomyelin. S1 is at the front of brain and S5 is at the back of brain.
Figure 2:
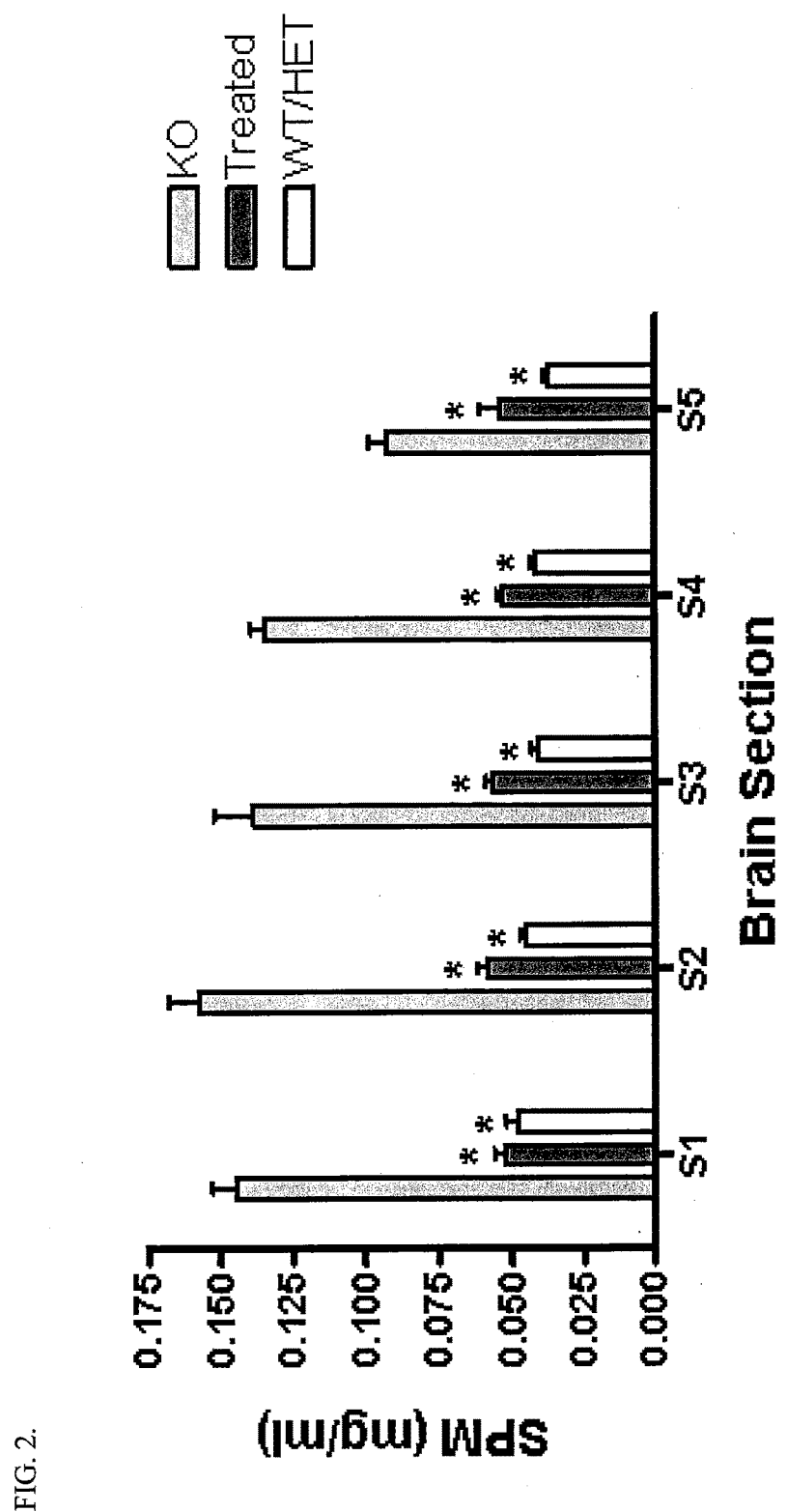
FIG. 2 shows that intraventricular administration of rhASM reduces SPM levels in the ASMKO mouse brain.
Figure 4:
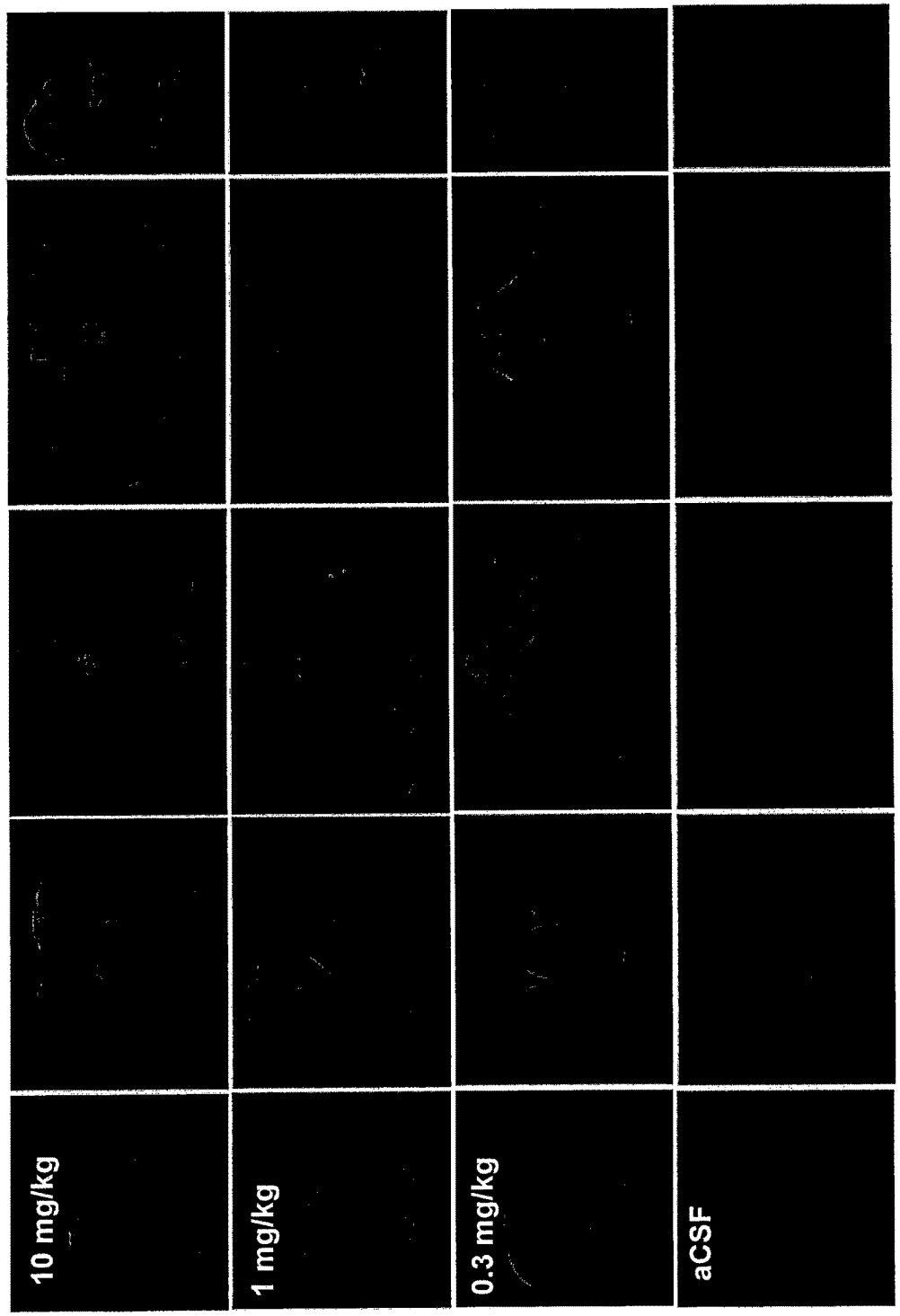
FIG. 4 shows hASM staining in the brain following intraventricular infusion.
Figure 5:
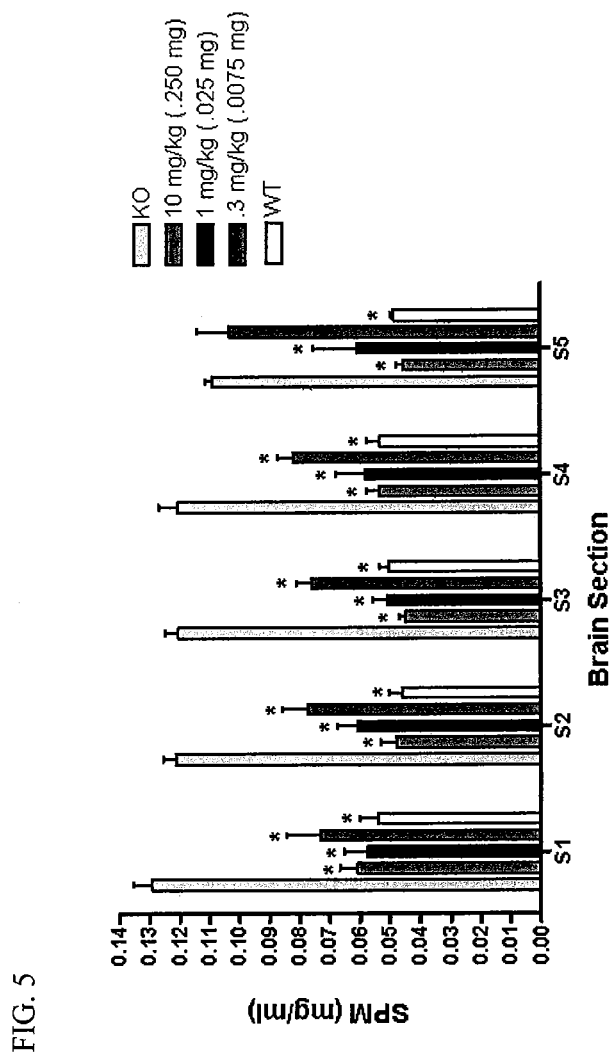
FIG. 5 shows that intraventricular infusion of rhASM over a 6 h period reduces SPM levels in the ASMKO mouse brain.
Figure 8:
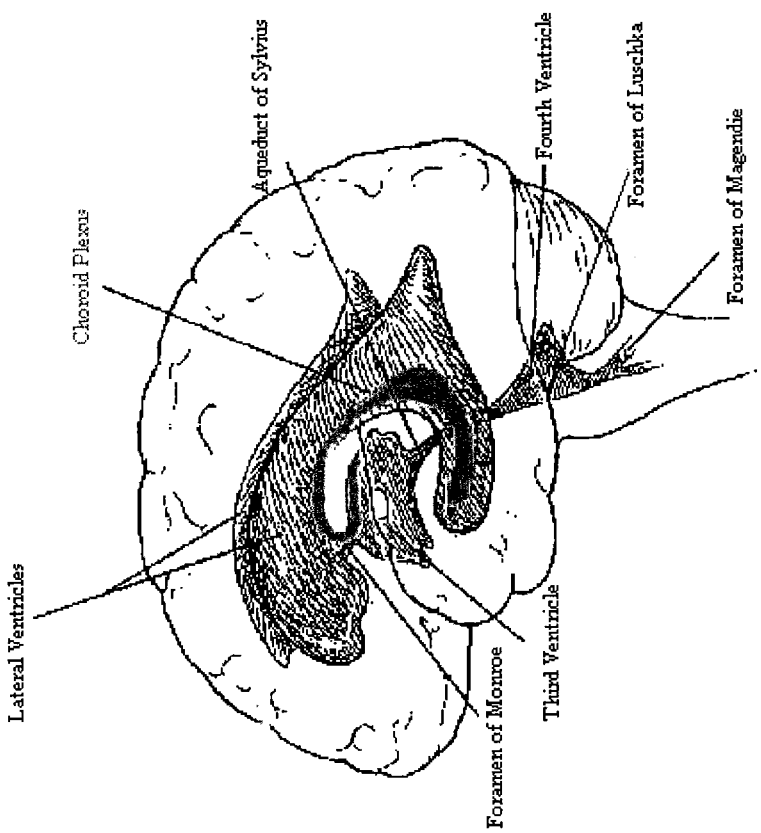
FIG. 8 shows a cross section view of the brain with the ventricles indicated.
Figure 9A:
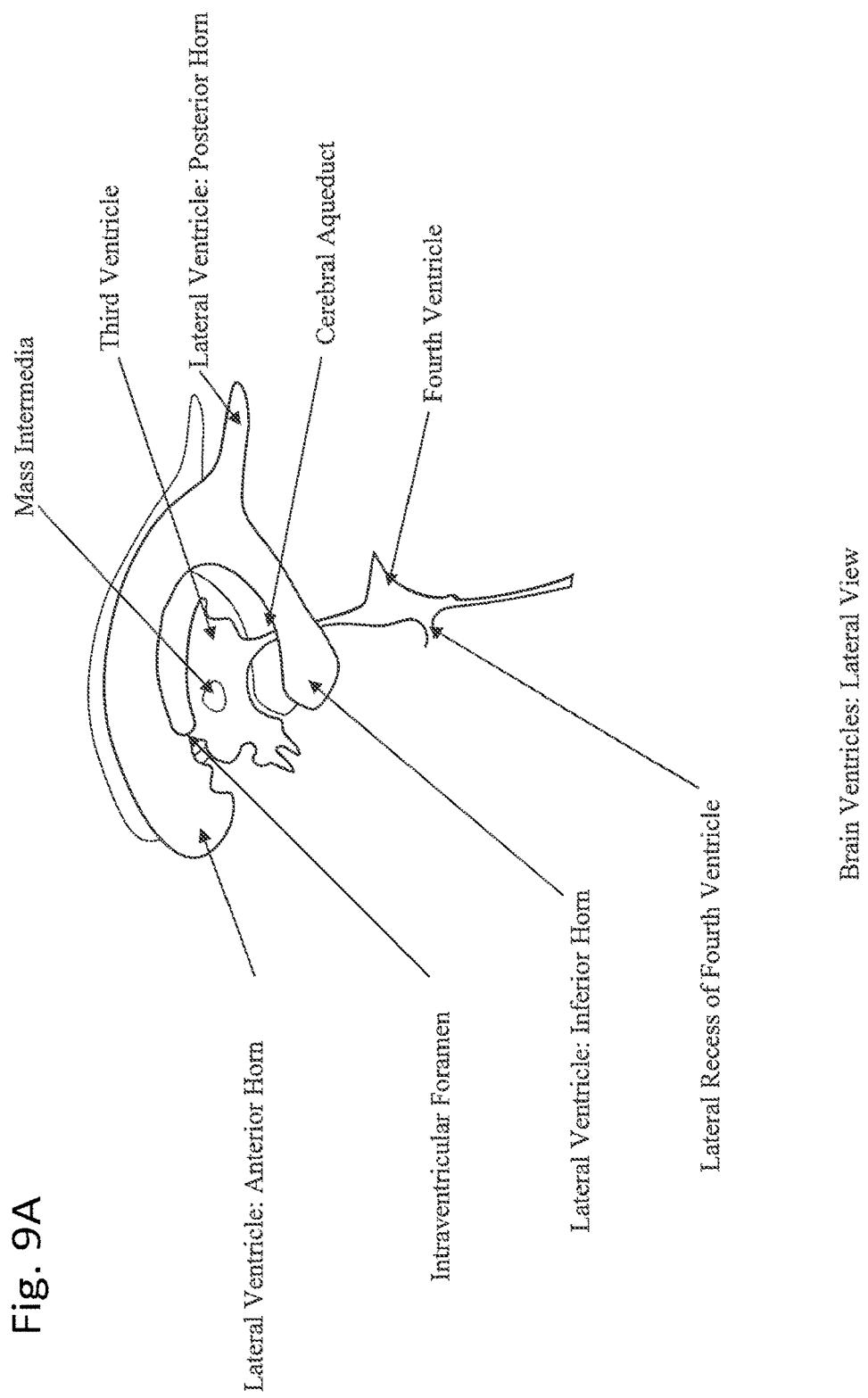
FIGS. 9A and 9B show lateral and superior views, respectively, of the ventricles.
Figure 9B:
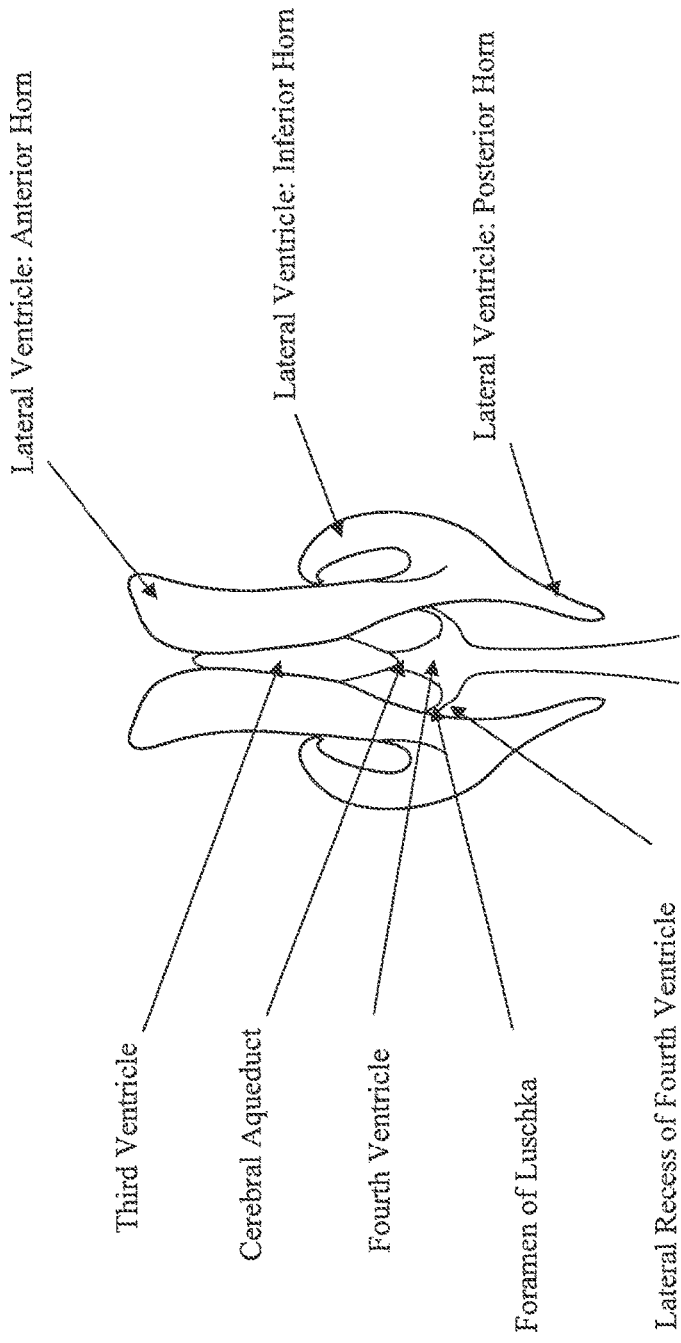
Figure 10:
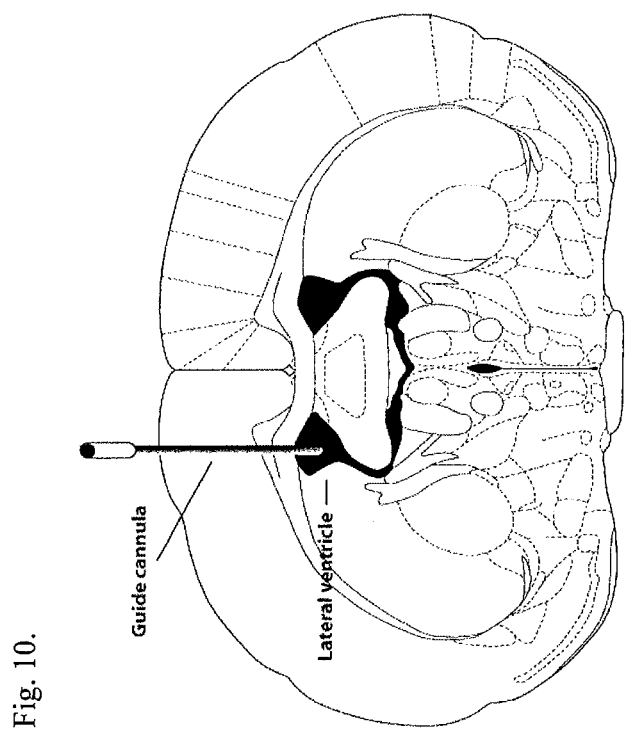
FIG. 10 shows injection into the lateral ventricles.

The practice of the present invention will employ, unless otherwise indicated, conventional techniques of immunology, molecular biology, microbiology, cell biology and recombinant DNA, which are within the skill of the art. See, e.g., Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

As used in the specification and claims, the singular forms "a," "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and excluding substantial method steps for administering the compositions or medicaments in accordance with this invention. Embodiments defined by each of these transition terms are within the scope of this invention.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about." It also is to be understood, although not always explicitly stated, that the reagents described herein are merely exemplary and that equivalents of such that are known in the art may also be used.

The terms "therapeutic," "therapeutically effective amount," and their cognates refer to that amount of a substance, e.g., enzyme or protein, that results in prevention or delay of onset, or amelioration, of one or more symptoms of a disease in a subject, or an attainment of a desired biological outcome, such as correction of neuropathology. The term "therapeutic correction" refers to that degree of correction which results in prevention or delay of onset, or amelioration, of one or more symptoms in a subject. The effective amount can be determined by known empirical methods.

A "composition" or "medicament" is intended to encompass a combination of an active agent, e.g., an enzyme, and a carrier or other material, e.g., a compound or composition, which is inert (for example, a detectable agent or label) or active, such as an adjuvant, diluent, binder, stabilizer, buffer, salt, lipophilic solvent, preservative, adjuvant or the like, or a mixture of two or more of these substances. Carriers are preferably pharmaceutically acceptable. They may include pharmaceutical excipients and additives, proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term carrier also includes a buffer or a pH adjusting agent or a composition containing the same; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid, Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions and medicaments which are manufactured and/or used in accordance with the present invention and which include the particular enzyme whose deficiency is to be corrected can include stabilizers and preservatives and any of the above noted carriers with the additional proviso that they be acceptable for use in vivo. For examples of carriers, stabilizers and adjuvants, see Martin REMINGTON'S PHARM. SCI., 15th Ed. (Mack Publ. Co., Easton (1975) and Williams & Williams, (1995), and in the "PHYSICIAN'S DESK REFERENCE", $52^{nd}$ ed., Medical Economics, Montvale, N.J. (1998).

A "subject," "individual" or "patient" is used interchangeably herein, which refers to a vertebrate, preferably a mammal, more preferably a human. Mammals include, but are not limited to, mice, rats, monkeys, humans, farm animals, sport animals, and pets.

As used herein, the term "modulate" means to vary the amount or intensity of an effect or outcome, e.g., to enhance, augment, diminish or reduce.

As used herein the term "ameliorate" is synonymous with "alleviate" and means to reduce or lighten. For example, one may ameliorate the symptoms of a disease or disorder by making them more bearable.

For identification of structures in the human brain, see, e.g., The Human Brain: Surface, Three-Dimensional Sectional Anatomy With MRI, and Blood Supply, 2nd ed., eds. Deuteron et al., Springer Vela, 1999; Atlas of the Human Brain, eds. Mai et al., Academic Press; 1997; and Co-Planar Stereotaxic Atlas of the Human Brain: 3-Dimensional Proportional System: An Approach to Cerebral Imaging, eds. Tamarack et al., Thyme Medical Pub., 1988. For identification of structures in the mouse brain, see, e.g., The Mouse Brain in Stereotaxic Coordinates, 2nd ed., Academic Press, 2000.

The inventors have discovered that intraventricular delivery to the brain of lysosomal hydrolase enzymes to patients who are deficient in the enzymes, leads to improved metabolic status of both the brain and the affected visceral (non-CNS) organs. This is particularly true when the delivery rate is slow, relative to a bolus delivery. Lysosomal storage diseases caused by a deficiency in a particular enzyme, such as those diseases identified in Table 1 above, may therefore be treated or prevented by the intraventricular administration of the respective enzyme. One particularly useful enzyme for treating Niemann-Pick A or B is acid sphingomyelinase (ASM), such as that shown in SEQ ID NO: 1.[1] One particularly useful enzyme for treating Gaucher disease is glucocerebrosidase. One particularly useful enzyme for treating MPS I disease is alpha-L-Iduronidase. One particularly useful enzyme for treating MPS II disease is iduronate-2-sulfatase. One particularly useful enzyme for treating Pompe disease, or glycogen storage disease type II (GSDII), also termed acid maltase deficiency (AMD) is acid alpha-glucosidase. One particularly useful enzyme for treating classic late infantile Batten disease (CLN2) is tripeptidyl peptidase. The enzymes that are used and/or administered in accordance with the present invention may be recombinant forms of the enzymes which are produced using methods that are well-known in the art. In one embodiment, the enzyme is a recombinant human enzyme.

Residues 1-46 constitute the signal sequence which is cleaved upon secretion.

Administration of lysosomal enzymes, and more particularly lysosomal hydrolase enzymes, to patients who are deficient in the enzymes may be performed into any one or more of the brain's ventricles, which are filled with cerebrospinal fluid (CSF). CSF is a clear fluid that fills the ventricles, is present in the subarachnoid space, and surrounds the brain and spinal cord. CSF is produced by the choroid plexuses and via the weeping or transmission of tissue fluid by the brain into the ventricles. The choroid plexus is a structure lining the floor of the lateral ventricle and the roof of the third and fourth ventricles. Certain studies have indicated that these structures are capable of producing 400-600 ccs of fluid per day consistent with an amount to fill the central nervous system spaces four times in a day. In adults, the volume of this fluid has been calculated to be from 125 to 150 ml (4-5 oz). The CSF is in continuous formation, circulation and absorption. Certain studies have indicated that approximately 430 to 450 ml (nearly 2 cups) of CSF may be produced every day. Certain calculations estimate that production equals approximately 0.35 ml per minute in adults and 0.15 per minute in infants. The choroid plexuses of the lateral ventricles produce the majority of CSF. It flows through the foramina of Monro into the third ventricle where it is added to by production from the third ventricle and continues down through the aqueduct of Sylvius to the fourth ventricle. The fourth ventricle adds more CSF; the fluid then travels into the subarachnoid space through the foramina of Magendie and Luschka. It then circulates throughout the base of the brain, down around the spinal cord and upward over the cerebral hemispheres. The CSF empties into the blood via the arachnoid villi and intracranial vascular sinuses, thereby delivering the enzymes that are infused into the ventricles to not only the brain but also to the visceral organs that are known to be affected in LSDs.

Although a particular amino acid sequence is shown in SEQ ID NO: 1, variants of that sequence which retain activity, e.g., normal variants in the human population, can be used as well. Typically these normal variants differ by just one or two residues from the sequence shown in SEQ ID NO: 1. The variants of SEQ ID NO: 1 that are to be used in accordance with the present invention, whether naturally occurring or not, should be at least 95%, 96%, 97%, 98%, or 99% identical to SEQ ID NO: 1. Variants of other enzymes may be used in accordance with the present invention. However, irrespective of the enzyme that is used, variants which are associated with disease or reduced activity should not be used. Typically the mature form of the enzyme will be delivered. In the case of SEQ ID NO: 1, the mature form will begin with residue 47 as shown in SEQ ID NO: 1. Variants which are associated with disease are shown in FIG. 7. In a similar manner, normal variants in the human population of such LSD enzymes as glucocerebrosidase, alpha-L-Iduronidase, iduronate-2-sulfatase, acid alpha-glucosidase, and tripeptidyl peptidase that which retain enzymatic activity can be used as well.

Kits according to the present invention are assemblages of separate components. While they can be packaged in a single container, they can be subpackaged separately. Even a single container can be divided into compartments. Typically a set of instructions will accompany the kit and provide instructions for delivering the enzymes, e.g., the lysosomal hydrolase enzymes, intraventricularly. The instructions may be in printed form, in electronic form, as an instructional video or DVD, on a compact disc, on a floppy disc, on the internet with an address provided in the package, or a combination of these means. Other components, such as diluents, buffers, solvents, tape, screws, and maintenance tools can be provided in addition to the enzyme, one or more cannulae or catheters, and/or a pump.

The populations treated by the methods of the invention include, but are not limited to, patients having, or who are at risk for developing, a neurometabolic disorder, e.g., an LSD, such as the diseases listed in Table 1, particularly if such a disease affects the CNS and visceral organs. In an illustrative embodiment, the disease is type A Niemann-Pick disease.

An ASM or other lysosomal hydrolase enzyme can be incorporated into a pharmaceutical composition useful to treat, e.g., inhibit, attenuate, prevent, or ameliorate, a condition characterized by an insufficient level of a lysosomal hydrolase activity. The pharmaceutical composition will be administered to a subject suffering from a lysosomal hydrolase deficiency or someone who is at risk of developing said deficiency. The compositions should contain a therapeutic or prophylactic amount of the ASM or other lysosomal hydrolase enzyme, in a pharmaceutically-acceptable carrier. The pharmaceutical carrier can be any compatible, non-toxic substance suitable to deliver the polypeptides to the patient. Sterile water, alcohol, fats, and waxes may be used as the carrier. Pharmaceutically-acceptable adjuvants, buffering agents, dispersing agents, and the like, may also be incorporated into the pharmaceutical compositions. The carrier can be combined with the ASM or other lysosomal hydrolase enzyme in any form suitable for administration by intraventricular injection or infusion (which form is also possibly suitable for intravenous or intrathecal administration) or otherwise. Suitable carriers include, for example, physiological saline, bacteriostatic water, Cremophor EL™ (BASF, Parsippany, N.J.) or phosphate buffered saline (PBS), other saline solutions, dextrose solutions, glycerol solutions, water and oils emulsions such as those made with oils of petroleum, animal, vegetable, or synthetic origin (peanut oil, soybean oil, mineral oil, or sesame oil). An artificial CSF can be used as a carrier. The carrier will preferably be sterile and free of pyrogens. The concentration of the ASM or other lysosomal hydrolase enzyme in the pharmaceutical composition can vary widely, i.e., from at least about 0.01% by weight, to 0.1% by weight, to about 1% weight, to as much as 20% by weight or more of the total composition.

For intraventricular administration of ASM or other lysosomal hydrolase enzyme, the composition must be sterile and should be fluid. It must be stable under the conditions of manufacture and storage and must be preserved against the contaminating action of microorganisms such as bacteria and fungi. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition.

Dosage of ASM or other lysosomal hydrolase enzyme may vary somewhat from individual to individual, depending on the particular enzyme and its specific in vivo activity, the route of administration, the medical condition, age, weight or sex of the patient, the patient's sensitivities to the ASM or other lysosomal hydrolase enzyme or components of the vehicle, and other factors which the attending physician will be capable of readily taking into account. While dosages may vary depending on the disease and the patient, the enzyme is generally administered to the patient in amounts of from about 0.1 to about 1000 milligrams per 50 kg of patient per month. In one embodiment, the enzyme is administered to the patient in amounts of about 1 to about 500 milligrams per 50 kg of patient per month. In other embodiments, the enzyme is administered to the patient in amounts of about 5 to about 300 milligrams per 50 kg of patient per month, or about 10 to about 200 milligrams per 50 kg of patient per month.

The rate of administration is such that the administration of a single dose may be administered as a bolus. A single dose may also be infused over about 1-5 minutes, about 5-10 minutes, about 10-30 minutes, about 30-60 minutes, about 1-4 hours, or consumes more than four, five, six, seven, or eight hours. It may take more than 1 minute, more than 2 minutes, more than 5 minutes, more than 10 minutes, more than 20 minutes, more than 30 minutes, more than 1 hour, more than 2 hours, or more than 3 hours. Applicants have observed that, while bolus intraventricular administration may be effective, slow infusion is very effective. While applicants do not wish to be bound by any particular theory of operation, it is believed that the slow infusion is more effective due to the turn-over of the cerebrospinal fluid (CSF). While estimates and calculations in the literature vary, the cerebrospinal fluid is believed to turn over within about 4, 5, 6, 7, or 8 hours in humans. In one embodiment, the slow infusion time of the invention should be metered so that it is about equal to or greater than the turn-over time of the CSF. Turn-over time may depend on the species, size, and age of the subject but may be determined using methods known in the art. Infusion may also be continuous over a period of one or more days. The patient may be treated once, twice, or three or more times a month, e.g., weekly, e.g. every two weeks. Infusions may be repeated over the course of a subject's life as dictated by re-accumulation of the disease's substrate in the brain or visceral organs. Re-accumulation may be determined by any of the techniques that are well known in the art for the identification and quantization of the relevant substrate, which techniques may be performed on one or more samples taken from the brain and/or from one or more of the visceral organs. Such techniques include enzymatic assays and/or immunoassays, e.g. radioimmunoassays or ELISAs.

The CSF empties into the blood via the arachnoid villi and intracranial vascular sinuses, thereby delivering the infused enzymes to the visceral organs that are known to be affected in LSDs. The visceral organs which are often affected in Niemann-Pick disease are the lungs, spleen, kidney, and liver. The slow intraventricular infusion provides diminished amounts of the substrate for an administered enzyme in at least the brain and potentially in visceral organs. The reduction in substrate accumulated in the brain, lungs, spleen, kidney, and/or liver may be dramatic. Reductions of greater that 10%, 20%, 30%, 40%, 50%, 60%, 70%, 80%, 90% can be achieved. The reduction achieved is not necessarily uniform from patient to patient or even from organ to organ within a single patient. Reductions can be determined by any of the techniques that are well known in the art, e.g., by enzymatic assays and/or immunoassay techniques, as discussed elsewhere herein.

If desired, the human brain structure can be correlated to similar structures in the brain of another mammal. For example, most mammals, including humans and rodents, show a similar topographical organization of the entorhinal-hippocampus projections, with neurons in the lateral part of both the lateral and medial entorhinal cortex projecting to the dorsal part or septal pole of the hippocampus, whereas the projection to the ventral hippocampus originates primarily from neurons in medial parts of the entorhinal cortex (Principles of Neural Science, 4th ed., eds Kandel et al., McGraw-Hill, 1991; The Rat Nervous System, 2nd ed., ed. Paxinos, Academic Press, 1995). Furthermore, layer II cells of the entorhinal cortex project to the dentate gyrus, and they terminate in the outer two-thirds of the molecular layer of the dentate gyrus. The axons from layer III cells project bilaterally to the cornu ammonis areas CA1 and CA3 of the hippocampus, terminating in the stratum lacunose molecular layer.

In an illustrative embodiment, the administration is accomplished by infusion of the LSD enzyme into one or both of the lateral ventricles of a subject or patient. By infusing into the lateral ventricles, the enzyme is delivered to the site in the brain in which the greatest amount of CSF is produced. The enzyme may also be infused into more than one ventricle of the brain. Treatment may consist of a single infusion per target site, or may be repeated. Multiple infusion/injection sites can be used. For example, the ventricles into which the enzyme is administered may include the lateral ventricles and the fourth ventricle. In some embodiments, in addition to the first administration site, a composition containing the LSD enzyme is administered to another site which can be contralateral or ipsilateral to the first administration site. Injections/infusions can be single or multiple, unilateral or bilateral.

To deliver the solution or other composition containing the enzyme specifically to a particular region of the central nervous system, such as to a particular ventricle, e.g., to the lateral ventricles or to the fourth ventricle of the brain, it may be administered by stereotaxic microinjection. For example, on the day of surgery, patients will have the stereotaxic frame base fixed in place (screwed into the skull). The brain with stereotaxic frame base (MRI-compatible with fiduciary markings) will be imaged using high resolution MRI. The MRI images will then be transferred to a computer that runs stereotaxic software. A series of coronal, sagittal and axial images will be used to determine the target site of vector injection, and trajectory. The software directly translates the trajectory into 3-dimensional coordinates appropriate for the stereotaxic frame. Burr holes are drilled above the entry site and the stereotaxic apparatus localized with the needle implanted at the given depth. The enzyme solution in a pharmaceutically acceptable carrier will then be injected. Additional routes of administration may be used, e.g., superficial cortical application under direct visualization, or other non-stereotaxic application.

One way for delivering a slow infusion is to use a pump. Such pumps are commercially available, for example, from Alzet (Cupertino, Calif.) or Medtronic (Minneapolis, Minn.). The pump may be implantable. Another convenient way to administer the enzymes is to use a cannula or a catheter. The cannula or catheter may be used for multiple administrations separated in time. Cannulae and catheters can be implanted stereotaxically. It is contemplated that multiple administrations will be used to treat the typical patient with a lysosomal storage disease. Catheters and pumps can be used separately or in combination.

The lysosomal storage diseases (LSD) includes over forty genetic disorders, many of which involve genetic defects in various lysosomal hydrolases. Representative lysosomal storage diseases and the associated defective enzymes are listed in Table 1.

Gaucher disease results as a consequence of an inherited deficiency of the lysosomal hydrolase glucocerebrosidase (GC), leading to the accumulation of its substrate, glucosylceramide (GL-1), in the lysosomes of histiocytes. The progressive accumulation of GL-1 in tissue macrophages (Gaucher cells) occurs in various tissues. The extent of the accumulation is dependent in part on the genotype. Clinically, three different Gaucher phenotypes are recognized, the non-neuropathic type 1, which is the most common with onset ranging from early childhood to adulthood, and the neuropathic types 2 and 3, presenting in infancy and early childhood, respectively. Any of these phenotypes may be treated in accordance with the present invention. The primary clinical manifestations common to all forms of Gaucher disease are hepatosplenomegaly, cytopenia, pathological bone fractures and, occasionally, pulmonary failure. A detailed discussion of Gaucher disease may be found in the Online Metabolic & Molecular Bases of Inherited Diseases, Part 16, Chapter 146 and 146.1 (2007). In patients with type 2 and type 3 Gaucher disease in whom there is significant central nervous system involvement, intraventricular delivery of the defective LSD enzyme leads to improved metabolic status of the brain and potentially the affected visceral (non-CNS) organs. Intraventricular delivery of the defective LSD enzyme in subjects with Gaucher type 1 disease leads to improved metabolic status of affected visceral (non-CNS) organs. There are animal models of Gaucher disease, which have derived from mouse models created by targeted disruption of the corresponding mouse gene. For example, a Gaucher mouse model harboring the D409V mutation in the mouse GC locus exists (Xu, Y-H et al. (2003). Am. J. Pathol. 163:2093-2101). The heterozygous mouse, gbaD409V/null, exhibits □5% of normal GC activity in visceral tissues and develops lipid-engorged macrophages (Gaucher cells) in the liver, spleen, lung and bone marrow by 4 months of age. This model is a suitable system in which to evaluate the benefits of and to determine the conditions for the intraventricular delivery of the defective LSD enzyme in subjects with Gaucher disease.

Niemann-Pick disease (NPD) is a lysosomal storage disease and is an inherited neurometabolic disorder characterized by a genetic deficiency in acid sphingomyelinase (ASM; sphingomyelin cholinephosphohydrolase, EC 3.1.3.12). The lack of functional ASM protein results in the accumulation of sphingomyelin substrate within the lysosomes of neurons and glia throughout the brain. This leads to the formation of large numbers of distended lysosomes in the perikaryon, which are a hallmark feature and the primary cellular phenotype of type A NPD. The presence of distended lysosomes correlates with the loss of normal cellular function and a progressive neurodegenerative course that leads to death of the affected individual in early childhood (The Metabolic and Molecular Bases of Inherited Diseases, eds. Scriver et al., McGraw-Hill, New York, 2001, pp. 3589-3610). Secondary cellular phenotypes (e.g., additional metabolic abnormalities) are also associated with this disease, notably the high level accumulation of cholesterol in the lysosomal compartment. Sphingomyelin has strong affinity for cholesterol, which results in the sequestering of large amounts of cholesterol in the lysosomes of ASMKO mice and human patients (Leventhal et al. (2001) J. Biol. Chem., 276:44976-44983; Slotte (1997) Subcell. Biochem., 28:277-293; and Viana et al. (1990) J. Med. Genet., 27:499-504.) A detailed discussion of NPD disease may be found in the Online Metabolic & Molecular Bases of Inherited Diseases, Part 16, Chapter 144 (2007). There are animal models of NPD. For example, ASMKO mice are an accepted model of types A and B Niemann-Pick disease (Horinouchi et al. (1995) Nat. Genetics, 10:288-293; Jin et al. (2002) J. Clin. Invest., 109:1183-1191; and Otterbach (1995) Cell, 81:1053-1061). Intraventricular delivery of the defective LSD enzyme leads to improved metabolic status of the brain and the affected visceral (non-CNS) organs.

Mucopolysaccharidoses (MPS) are a group of lysosomal storage disorders caused by deficiencies of enzymes catalyzing the degradation of glycosaminoglycans (mucopolysaccharides). There are 11 known enzyme deficiencies that give rise to 7 distinct MPS, including MPS I (Hurler, Scheie, and Hurler-Scheie Syndromes) and MPS II (Hunter Syndrome). Any MPS can be treated in accordance with the present invention. A detailed discussion of MPS may be found in the Online Metabolic & Molecular Bases of Inherited Diseases, Part 16, Chapter 136 (2007). There are numerous animal models of MPS, which have derived from naturally occurring mutations in dogs, cats, rats, mice, and goats, as well as mouse models created by targeted disruption of the corresponding mouse gene. The biochemical and metabolic features of these animal models are generally quite similar to those found in humans; however, the clinical presentations may be milder. For example, accepted models for MPS I include a murine model [Clark, L A et al., Hum. Mol. Genet. (1997), 6:503] and a canine model [Menon, K P et al., Genomics (1992), 14:763. For example, accepted models for MPS II include a mouse model [Muenzer, J. et al., (2002), Acta Paediatr. Suppl.; 91(439):98-9]. In the MPS that have central nervous system involvement, such as is found in patients with MPS I and MPS II, intraventricular delivery of the defective LSD enzyme leads to improved metabolic status of the brain and potentially the affected visceral (non-CNS) organs.

Pompe disease, or glycogen storage disease type II (GS-DII), also termed acid maltase deficiency (AMD) is an inherited disorder of glycogen metabolism resulting from defects in activity of the lysosomal hydrolase acid alpha-glucosidase in all tissues of affected individuals. The enzyme deficiency results in intralysosomal accumulation of glycogen of normal structure in numerous tissues. The accumulation is most marked in cardiac and skeletal muscle and in hepatic tissues of infants with the generalized disorder. In late-onset GSDII, intralysosomal accumulation of glycogen is virtually limited to skeletal muscle and is of lesser magnitude. Electromyographic abnormalities suggestive of the diagnosis include pseudomyotonic discharges and irritability, but in juvenile- and adult-onset patients, the abnormalities can vary in different muscles. CAT scans can reveal the site(s) of affected muscles. Most patients have elevated blood plasma levels of creatine kinase (CK) and elevations in hepatic enzymes, particularly in adult-onset patients, can be found. There are several naturally occurring animal models of the infantile- and late-onset disease. There is a knockout mouse model [Bijvoet A G et al., Hum. Mol. Genet. (1998); 7:53-62.]. Ameliorative effects of enzyme therapy have been described in knockout mice [Raben, N et al., Mol. Genet. Metab. (2003); 80:159-69] and in a quail model. Intraventricular delivery of the defective LSD enzyme leads to improved metabolic status of the brain and potentially the affected visceral (non-CNS) organs.

The neuronal ceroid lipofuscinoses (NCL) are a group of neurodegenerative disorders distinguished from other neurodegenerative diseases by the accumulation of autofluorescent material ("aging pigment") in the brain and other tissues. The major clinical features include seizures, psychomotor deterioration, blindness, and premature death. Distinct subgroups of NCL have been recognized that differ in the age of onset of symptoms and the appearance of the storage material by electron microscopy. Three major groups-infantile (INCL), classical late infantile (LINCL), and juvenile (JNCL, also referred to as Batten disease)-are caused by autosomal recessive mutations in the CLN1, CLN2, and CLN3 genes, respectively. The protein products of the CLN1 (palmitoyl-protein thioesterase) and CLN2 (tripeptidyl peptidase or pepinase) genes are soluble lysosomal enzymes, whereas the CLN3 protein (battenin) is a lysosomal membrane protein, as is (tentatively) the CLN5 protein. The identification of mutations in genes encoding lysosomal proteins in several forms of NCL has led to the recognition of the lipofuscinoses as true lysosomal storage disorders. Any subgroup of NCL can be treated in accordance with the present invention. A detailed discussion of NCL disease may be found in the Online Metabolic & Molecular Bases of Inherited Diseases, Part 16, Chapter 154 (2007). Naturally occurring NCL disorders have been described in the sheep, dog, and mouse models have been derived by targeted disruption of a corresponding mouse gene [see e.g., Katz, M L et al., J. Neurosci. Res. (1999); 57:551-6; Cho, S K et al., Glycobiology (2005); 15:637-48.] Intraventricular delivery of the defective LSD enzyme leads to improved metabolic status of the brain and possibly the affected visceral (non-CNS) organs.

A detailed discussion of additional lysosomal storage disorders disclosed in Table 1, in which intraventricular delivery of the defective LSD enzyme in the disease, may be found in the Online Metabolic & Molecular Bases of Inherited Diseases, Part 16 (2007).

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

Animal Model

ASMKO mice are an accepted model of types A and B Niemann-Pick disease (Horinouchi et al. (1995) Nat. Genetics, 10:288-293; Jin et al. (2002) J. Clin. Invest., 109:1183-1191; and Otterbach (1995) Cell, 81:1053-1061). Niemann-Pick disease (NPD) is classified as a lysosomal storage disease and is an inherited neurometabolic disorder characterized by a genetic deficiency in acid sphingomyelinase (ASM; sphingomyelin cholinephosphohydrolase, EC 3.1.3.12). The lack of functional ASM protein results in the accumulation of sphingomyelin substrate within the lysosomes of neurons and glia throughout the brain. This leads to the formation of large numbers of distended lysosomes in the perikaryon, which are a hallmark feature and the primary cellular phenotype of type A NPD. The presence of distended lysosomes correlates with the loss of normal cellular function and a progressive neurodegenerative course that leads to death of the affected individual in early childhood (The Metabolic and Molecular Bases of Inherited Diseases, eds. Scriver et al., McGraw-Hill, New York, 2001, pp. 3589-3610). Secondary cellular phenotypes (e.g., additional metabolic abnormalities) are also associated with this disease, notably the high level accumulation of cholesterol in the lysosomal compartment. Sphingomyelin has strong affinity for cholesterol, which results in the sequestering of large amounts of cholesterol in the lysosomes of ASMKO mice and human patients (Leventhal et al. (2001) J. Biol. Chem., 276:44976-44983; Slotte (1997) Subcell. Biochem., 28:277-293; and Viana et al. (1990) J. Med. Genet., 27:499-504.)

EXAMPLE 2

"Continuous Intraventricular Infusion of RhASM in the ASMKO Mouse"

Goal: To determine what effect intraventricular infusion of recombinant human ASM (rhASM) has on storage pathology (i.e., sphingomyelin and cholesterol storage) in the ASMKO mouse brain Methods: ASMKO mice were stereotaxically implanted with an indwelling guide cannula between 12 and 13 weeks of age. At 14 weeks of age mice were infused with 0.250 mg of hASM (n=5) over a 24 h period (~0.01 mg/h) for four straight days (1 mg total was administered) using an infusion probe (fits inside the guide cannula) which is connected to a pump. Lyophilized hASM was dissolved in artificial cerebral spinal fluid (aCSF) prior to infusion. Mice were sacrificed 3 days post infusion. At sacrifice mice were overdosed with euthasol (>150 mg/kg) and then perfused with PBS or 4% parformaldehyde. Brain, liver, lung and spleen were removed and analyzed for sphingomyelin (SPM) levels. Brain tissue was divided into 5 sections before SPM analysis (S1=front of brain, S5=back of the brain; see FIG. 1)

TABLE 2

| Group | Treatment | n |
|---|---|---|
| ASMKO | .250 mg/24 h (1 mg total) | 5 |
| ASMKO | None | 4 |
| WT | None | 4 |

Results summary: Intraventricular infusion of hASM at 0.250mg/24 h for 4 continuous days (1 mg total) resulted in hASM staining and filipin (i.e., cholesterol storage) clearance throughout the ASMKO brain. Biochemical analysis showed that intraventricular infusion of hASM also led to a global reduction in SPM levels throughout the brain. SPM levels were reduced to that of wild type (WT) levels. A significant reduction in SPM was also observed in the liver and spleen (a downward trend was seen in the lung).

EXAMPLE 3

"Intraventricular Delivery of HASM in ASMKO Mice II"

Goal: to determine lowest efficacious dose over a 6 h infusion period.

Methods: ASMKO mice were stereotaxically implanted with an indwelling guide cannula between 12 and 13 weeks of age. At 14 weeks of age mice were infused over a 6 hour period at one of the following doses of hASM: 10 mg/kg (0.250 mg; n=12), 3 mg/kg (0.075 mg; n=7), 1 mg/kg (0.025 mg; n=7), 0.3 mg/kg (0.0075 mg; n=7), or aCSF (artificial cerebral spinal fluid; n=7). Two mice from each dose level were perfused with 4% parformaldehyde immediately following the 6 h infusion to assess enzyme distribution in the brain (blood was also collected from these to determine serum hASM levels). The remaining mice from each group were sacrificed 1 week post infusion. Brain, liver, and lung tissue from these mice was analyzed for SPM levels as in study 05-0208.

TABLE 3

| Group | Treatment | n |
|---|---|---|
| ASMKO | 0.250 mg (10 mg/kg) | 12 |
| ASMKO | 0.075 mg (3 mg/kg) | 7 |
| ASMKO | 0.025 mg (1 mg/kg) | 7 |
| ASMKO | 0.0075 mg (.3 mg/kg) | 7 |
| ASMKO | aCSF | 7 |
| WT | None | 7 |

Results summary: Intraventricular hASM over a 6h period led to a significant reduction in SPM levels throughout the brain regardless of dose. Brain SPM levels in mice treated with doses >0.025 mg were reduced to WT levels. Visceral organ SPM levels were also significantly reduced (but not to WT levels) in a dose dependent manner. In support of this finding hASM protein was also detected in the serum of ASMKO mice infused with hASM protein. Histological analysis showed that hASM protein was widely distributed throughout the brain (from S1 to S5) after intraventricular administration of hASM.

EXAMPLE 4

"Intraventricular Infusion of RhASM in ASMKO Mice III"

Goal: To determine (1) the time it takes for SPM to reaccumulate within the brain (and spinal cord) after a 6 h infusion of hASM (dose=0.025 mg); (2) if there are sex differences in response to intraventricular hASM administration (pervious experiments demonstrate that there are sex differences in substrate accumulation in the liver, whether or not this occurs in the brain is unknown).

Methods: ASMKO mice were stereotaxically implanted with an indwelling guide cannula between 12 and 13 weeks of age. At 14 weeks of age mice were infused over a 6 h period with 0.025 mg of hASM. After intraventricular delivery of hASM mice were sacrificed either at 1 week post infusion (n=7 males, 7 females), or at 2 weeks post infusion (n=7 males, 7 females) or at 3 weeks post infusion (n=7 males, 7 females). At sacrifice the brain, spinal cord, liver and lung were removed for SPM analysis.

TABLE 4

| Group | Treatment | N | Sacrifice |
|---|---|---|---|
| male ASMKO | .025 mg | 7 | 1 week post infusion |
| Female ASMKO | .025 mg | 7 | 1 week post infusion |
| male ASMKO | .025 mg | 7 | 2 weeks post infusion |
| Female ASMKO | .025 mg | 7 | 2 weeks post infusion |
| male ASMKO | .025 mg | 7 | 3 weeks post infusion |

TABLE 4-continued

| Group | Treatment | N | Sacrifice |
|---|---|---|---|
| Female ASMKO | .025 mg | 7 | 3 weeks post infusion |
| male ASMKO | aCSF | 7 | 1 week post infusion |
| Female ASMKO | aCSF | 7 | 1 week post infusion |
| male WT | None | 7 | 1 week post infusion |
| Female WT | None | 7 | 1 week post infusion |

Tissue samples are prepared for SPM analysis.

EXAMPLE 5

"Effect of Intraventricular Infusion of RhASM on Cognitive Function in ASMKO Mice"

Goal: to determine if intraventricular infusion of rhASM alleviates diseased induced cognitive deficits in ASMKO mice Methods: ASMKO mice are stereotaxically implanted with an indwelling guide cannula between 9 and 10 weeks of age. At 13 weeks of age mice are infused over a 6 h period with 0.025 mg of hASM. At 14 and 16 weeks of age mice undergo cognitive testing using the Barnes maze.

EXAMPLE 6

"HASM Protein Distribution within the ASMKO CNS after Intraventricular Infusion"

Goal: to determine the distribution of hASM protein (as function of time) within the brain and spinal cord of ASMKO mice after intraventricular infusion Methods: ASMKO mice are stereotaxically implanted with an indwelling guide cannula between 12 and 13 weeks of age. At 14 weeks of age mice are infused over a 6 h period with 0.025 mg of hASM. Following infusion procedure mice are either sacrificed immediately or 1 week or 2 weeks or 3 weeks later.

TABLE 5

Indicates the infusion times that may be used with a particular enzyme for the treatment of the disease in which it is deficient as indicated in Table 1.
INFUSION TIME

| Enzyme for Infusion | BOLUS | 1-5 min | 5-10 min | 10-30 min | 30-60 min | 1-4 hrs | more than 4 hrs | more than 5 hrs | more than 6 hrs | more than 7 hrs | more than 8 hrs |
|---|---|---|---|---|---|---|---|---|---|---|---|
| Aspartylglucosaminidase.alpha.-Galactosidase A | X | X | X | X | X | X | X | X | X | X | X |
| Palmitoyl Protein Thioesterase | X | X | X | X | X | X | X | X | X | X | X |
| Tripeptidyl Peptidase | X | X | X | X | X | X | X | X | X | X | X |
| Lysosomal Transmembrane Protein | X | X | X | X | X | X | X | X | X | X | X |
| Cysteine transporter | X | X | X | X | X | X | X | X | X | X | X |
| Acid ceramidase | X | X | X | X | X | X | X | X | X | X | X |
| Acid.alpha.-L-fucosidase | X | X | X | X | X | X | X | X | X | X | X |
| Protective protein/cathepsin A | X | X | X | X | X | X | X | X | X | X | X |
| Acid.beta.-glucosidase, or Acid.beta.-galactosidase | X | X | X | X | X | X | X | X | X | X | X |
| Iduronate-2-sulfatase | X | X | X | X | X | X | X | X | X | X | X |
| alpha.L-Iduronidase | X | X | X | X | X | X | X | X | X | X | X |
| Galactocerebrosidase | X | X | X | X | X | X | X | X | X | X | X |
| Acid.alpha.-mannosidase | X | X | X | X | X | X | X | X | X | X | X |
| Acid.beta.-mannosidase | X | X | X | X | X | X | X | X | X | X | X |
| Arylsulfatase B | X | X | X | X | X | X | X | X | X | X | X |
| Arylsulfatase A | X | X | X | X | X | X | X | X | X | X | X |
| N-Acetylgalactosamine-6-sulfate | X | X | X | X | X | X | X | X | X | X | X |
| Acid.beta.-galactosidase | X | X | X | X | X | X | X | X | X | X | X |
| N-Acetylglucosamine-1- | X | X | X | X | X | X | X | X | X | X | X |
| Acid sphingomyelinase | X | X | X | X | X | X | X | X | X | X | X |

REFERENCES

The disclosure of each reference cited is expressly incorporated herein.

1) Belichenko P V, Dickson P I, Passage M, Jungles S, Mobley W C, Kakkis E D. Penetration, diffusion, and uptake of recombinant human alpha-l-iduronidase after intraventricular injection into the rat brain. Mol Genet Metab. 2005; 86(1-2):141-9.

2) Kakkis E, McEntee M, Vogler C, Le S, Levy B, Belichenko P, Mobley W, Dickson P, Hanson S, Passage M. Intrathecal enzyme replacement therapy reduces lysosomal storage in the brain and meninges of the canine model of MPS I. Mol Genet Metab. 2004; 83(1-2):163-74.

3) Bembi B, Ciana G, Zanatta M, et al. Cerebrospinal-fluid infusion of alglucerase in the treatment for acute neuronopathic Gaucher's disease. Pediatr Res 1995; 38:A425.

4) Lonser R R, Walbridge S, Murray G J, Aizenberg M R, Vortmeyer A O, Aerts J M, Brady R O, Oldfield E H. Convection perfusion of glucocerebrosidase for neuronopathic Gaucher's disease. Ann Neurol. 2005 April; 57(4):542-8.

---

We claim:

1. A method of treating a patient with Niemann-Pick A or Niemann-Pick B disease, comprising:
   administering a plurality of infusions of an acid sphingomyelinase to the patient via intraventricular delivery to the brain in an amount sufficient to reduce sphingomyelin levels throughout said brain; wherein each infusion is performed at a rate such that the administration of a single dose consumes more than four hours, and wherein the amount administered is sufficient to reduce at least 10% of sphingomyelin levels in the brain of the patient.

2. The method of claim 1 wherein the amount administered is sufficient to reduce sphingomyelin levels in the liver, lungs, spleen and/or kidney of the patient at least 10%.

3. The method of claim 1 wherein the amount administered is sufficient to reduce at least 20% of sphingomyelin levels in the brain of the patient.

4. The method of claim 3 wherein the amount administered is sufficient to reduce at least 30% sphingomyelin levels in the brain of the patient.

5. The method of claim 4 wherein the amount administered is sufficient to reduce at least 40% sphingomyelin levels in the brain of the patient.

6. The method of claim 5 wherein the amount administered is sufficient to reduce at least 50% sphingomyelin levels in the brain of the patient.

7. The method of claim 6 wherein the amount administered is sufficient to reduce at least 60% sphingomyelin levels in the brain of the patient.

8. The method of claim 1 wherein the step of administering employs a pump.

9. The method of claim 1 wherein the acid sphingomyelinase is administered via an indwelling catheter.

10. The method of claim 1 wherein the levels of sphingomyelin are monitored in the patient and additional acid sphingomyelinase is administered in response to the levels of sphingomyelin determined.

11. The method of claim 1 wherein the acid sphingomyelinase is a human acid sphingomyelinase.

12. The method of claim 1 wherein the acid sphingomyelinase shares at least 95% amino acid sequence identify with an acid sphingomyelinase as shown in SEQ ID NO:1.

13. The method of claim 1 wherein the acid sphingomyelinase has a sequence as shown in SEQ ID NO: 1.

14. The method of claim 1 wherein the step of administering a single dose is performed at a rate such that the administration of a single dose consumes more than five, six, seven or eight hours.

15. A method of treating a patient with a lysosomal storage disease which is caused by an enzyme deficiency that leads to an accumulation of the enzyme's substrate, the method comprising:
    administering a plurality of infusions of the enzyme to the patient via intraventricular delivery to the brain in an amount sufficient to reduce said enzyme's substrate levels throughout said brain; wherein each infusion is performed at a rate such that the administration of a single dose consumes more than two hours, and wherein the administration is such that at least 10% of the substrate levels throughout said brain of the patient are reduced.

16. The method of claim 15 wherein the lysosomal storage disease is Niemann-Pick A and the enzyme is acid sphingomyelinase.

17. The method of claim 15 wherein the lysosomal storage disease is
    a) Niemann-Pick B and the enzyme is acid sphingomyelinase,
    b) the lysosomal storage disease is Mucopolysaccharidosis I syndrome and the enzyme is alpha-L-iduronidase,
    c) the lysosomal storage disease is Mucopolysaccharidosis II syndrome and the enzyme is iduronate-2-sulfatase,
    d) the lysosomal storage disease is Gaucher disease and the enzyme is glucocerebrosidase,
    e) the lysosomal storage disease is Pompe disease and the enzyme is alpha-glucosidase, or
    f) the lysosomal storage disease is classic late infantile Batten disease (CLN2) and the enzyme is tripeptidyl peptidase.

18. The method of claim 15, wherein the enzyme is administered at a rate such that the administration of a single dose consumes more than three, four, five, six, seven, or eight hours.

19. The method of claim 1, wherein the plurality of infusions is administered to more than one ventricle of the brain.

20. The method of claim 19, wherein the more than one ventricle of the brain includes the lateral ventricles and the fourth ventricle.

21. The method of claim 15, wherein the plurality of infusions is administered to more than one ventricle of the brain.

22. The method of claim 21, wherein the more than one ventricle of the brain includes the lateral ventricles and the fourth ventricle.

* * * * *